(12) United States Patent
Aburada et al.

(10) Patent No.: US 11,051,985 B2
(45) Date of Patent: Jul. 6, 2021

(54) PREPARATION JIG FOR TYMPANIC MEMBRANE REGENERATING AGENT AND PREPARATION VESSEL FOR TYMPANIC MEMBRANE REGENERATING AGENT

(71) Applicant: Nobelpharma Co., Ltd., Tokyo (JP)

(72) Inventors: Takako Aburada, Tokyo (JP); Shinobu Yamada, Tokyo (JP)

(73) Assignee: Nobelpharma Co., Ltd., Tokyo (JP)

( * ) Notice: Subject to any disclaimer, the term of this patent is extended or adjusted under 35 U.S.C. 154(b) by 254 days.

(21) Appl. No.: 15/765,412

(22) PCT Filed: Sep. 30, 2016

(86) PCT No.: PCT/JP2016/079190
§ 371 (c)(1),
(2) Date: Apr. 2, 2018

(87) PCT Pub. No.: WO2017/057767
PCT Pub. Date: Apr. 6, 2017

(65) Prior Publication Data
US 2018/0280198 A1  Oct. 4, 2018

(30) Foreign Application Priority Data
Oct. 1, 2015 (JP) .............................. JP2015-196038

(51) Int. Cl.
*A61F 11/00* (2006.01)
*A61F 2/00* (2006.01)
(Continued)

(52) U.S. Cl.
CPC ............ *A61F 11/00* (2013.01); *A61F 2/0095* (2013.01); *A61M 31/002* (2013.01);
(Continued)

(58) Field of Classification Search
CPC .................... A61F 11/00; A61F 2/0095; A61F 2250/0067; A61M 31/002;
(Continued)

(56) References Cited

U.S. PATENT DOCUMENTS 4,182,446 A * 1/1980 Penny .................. A61F 2/0095
206/205
6,447,799 B1 * 9/2002 Ullman .................. A61L 15/32
128/DIG. 22
(Continued)

FOREIGN PATENT DOCUMENTS

| JP | 2007-119033 | 5/2007 |
| JP | 2007-159866 | 6/2007 |

(Continued)

OTHER PUBLICATIONS

International Search Report issued in International Application No. PCT/JP2016/079190, dated Jan. 31, 2017, 6 pages.

*Primary Examiner* — Don M Anderson
(74) *Attorney, Agent, or Firm* — Hamre, Schumann, Mueller & Larson, P.C.

(57) ABSTRACT

[Problem] The present invention provides a preparation jig for a tympanic membrane regenerating agent and a preparation vessel for a tympanic membrane regenerating agent enabling simple preparation of a tympanic membrane regenerating agent.
[Solution] A preparation jig for a tympanic membrane regenerating agent (1*a*) and a preparation vessel for a tympanic membrane regenerating agent (1A) each include: a vessel (3A) including housing walls (6, 7) forming an interior space (S1) housing a medicinal solution support (2), and including an opening (6*h*) opening in one direction and formed in the housing walls (6, 7); and a holding portion (4A) disposed in the interior space (S1). The deep side of the
(Continued)

interior space (S1) is a housing portion (S3) housing the medicinal solution support (2) holding a medicinal solution. The opening (6h) side of the interior space (S1) is an installation space (S2) in which the holding portion (4A) is disposed.

13 Claims, 11 Drawing Sheets

(51) Int. Cl.
    *A61M 31/00*     (2006.01)
    *A61K 9/00*     (2006.01)

(52) U.S. Cl.
    CPC ..... *A61F 2250/0067* (2013.01); *A61K 9/0046* (2013.01); *A61M 2210/0668* (2013.01)

(58) Field of Classification Search
    CPC ......... A61M 2210/0668; A61K 9/0046; B65D 1/34; B65D 65/38; B65D 65/42; B65D 2081/004; B65D 2081/002; B65D 2081/001; B65D 2081/008
    See application file for complete search history.

(56) References Cited

U.S. PATENT DOCUMENTS

| | | |
|---|---|---|
| 2011/0021964 A1 | 1/2011 | Larsen et al. |
| 2011/0110987 A1 | 5/2011 | Kanemaru |

FOREIGN PATENT DOCUMENTS

| | | |
|---|---|---|
| JP | 2008-044648 | 2/2008 |
| JP | 2011-513251 | 4/2011 |
| JP | 5398712 B | 1/2014 |
| WO | 2009/157558 | 12/2009 |

\* cited by examiner

PREPARATION JIG FOR TYMPANIC MEMBRANE REGENERATING AGENT AND PREPARATION VESSEL FOR TYMPANIC MEMBRANE REGENERATING AGENT

FIELD OF THE INVENTION

The present invention relates to a preparation jig for a tympanic membrane regenerating agent and a preparation vessel for a tympanic membrane regenerating agent.

BACKGROUND OF THE INVENTION

A tympanic membrane regenerating agent or the like described in, for example, Patent Literature 1 has been used in tympanic membrane regeneration therapy performed, for example, when the tympanic membrane has been perforated. The tympanic membrane regenerating agent described in Patent Literature 1 is prepared by incorporating a medicinal solution including a basic fibroblast growth factor (bFGF) and the like inside gelatin formed into a sponge form (referred to as a "gelatin sponge" hereinafter). Prior to the procedure, a practitioner puts the medicinal solution and the gelatin sponge in a Petri dish, gently holds the gelatin sponge to prevent the gelatin sponge from floating on the medicinal solution, and causes the gelatin sponge to absorb liquid, or uses a dropper or the like to cause the gelatin sponge to gradually absorb droplets of the medicinal solution. Furthermore, the practitioner turns the gelatin sponge over to enable uniform liquid absorption, and the practitioner holds the gelatin sponge down without squashing the gelatin sponge to cause degassing after a certain degree of liquid absorption.

PRIOR ART DOCUMENTS

Patent Documents

Patent Literature 1: JP 5398712 B

SUMMARY OF THE INVENTION

Problem to be Solved by Invention

However, there are a problem of inconvenient work in which the gelatin sponge has to be held at the time of liquid absorption, and furthermore, a problem of time and effort made to uniformly soak the gelatin sponge in the medicinal solution and hindering practitioners from performing any other work during that time.

Thus, an object of the present invention is to provide a preparation jig for a tympanic membrane regenerating agent and a preparation vessel for a tympanic membrane regenerating agent enabling convenient preparation of a tympanic membrane regenerating agent.

Means for Solving the Problem (1) A preparation jig for a tympanic membrane regenerating agent of the present invention includes: a vessel including housing walls forming an interior space housing a medicinal solution support, and including an opening opening in one direction and formed in the housing walls; and a holding portion disposed in the interior space, wherein a deep side of the interior space is a housing portion housing the medicinal solution support holding a medicinal solution, and the opening side of the interior space is an installation space in which the holding portion is disposed.

According to the preparation jig for a tympanic membrane regenerating agent of the present invention, the holding portion can prevent the medicinal solution support from moving when the medicinal solution support and the medicinal solution are put in the vessel.

(2) A passage may be formed in at least one of an inner wall face of the vessel and the holding portion, and a medicinal solution poured in from the opening in a state where the holding portion of the present invention is disposed in the installation space flows into the housing portion through the passage.

In the preparation jig for a tympanic membrane regenerating agent of the present invention, a medicinal solution can be poured into the housing portion through the passage in a state where the holding portion is disposed in the vessel.

(3) The vessel of the present invention may be provided with a lower side locking portion configured to restrict movement of the holding portion toward the housing portion side.

In the preparation jig for a tympanic membrane regenerating agent of the present invention, movement of the holding portion toward the housing portion side is restricted, and thus the holding portion can be prevented from inadvertently coming into contact with the medicinal solution support.

(4) The housing portion of the present invention may include a mounting portion on which the medicinal solution support is mounted, and a reservoir of a medicinal solution formed on the deep side of the mounting portion.

In the preparation jig for a tympanic membrane regenerating agent of the present invention, the medicinal solution is stored in the reservoir, and thus the medicinal solution support can absorb the medicinal solution not only from an upper face and side faces of the medicinal solution support, but also from a lower face of the medicinal solution support.

(5) The vessel may include an upper side locking portion configured to prevent movement of the holding portion of the present invention toward the opening side.

The preparation jig for a tympanic membrane regenerating agent of the present invention can conveniently suppress movement of the holding portion toward the opening side.

(6) A cover including a top plate covering the opening may be provided.

The preparation jig for a tympanic membrane regenerating agent of the present invention can prevent dust and the like from entering the vessel from the opening, and can keep the preparation jig for a tympanic membrane regenerating agent sanitary.

(7) The top plate of the present invention may include a concavity indented toward the installation space when the cover covers the vessel, and the concavity constitutes the holding portion.

In the preparation jig for a tympanic membrane regenerating agent of the present invention, the cover also functions to hold the holding portion, and thus a configuration of the preparation jig can be simplified.

(8) The vessel of the present invention may include a ring-shaped protruding wall further surrounding the interior space on the outside of the housing walls and protruding to the opening side; the cover may include a ring-shaped concavity formation wall forming, on a lower face side of the top plate, a ring-shaped concavity fitted onto the ring-shaped protruding wall; and the holding portion may be formed inward of the concavity formation wall.

Since the preparation jig for a tympanic membrane regenerating agent of the present invention includes the ring-shaped protruding wall on the outside of the housing walls of the vessel to form a so-called rib, rigidity of the housing walls can increase. Since the cover includes the ring-shaped concavity formation wall corresponding to the ring-shaped protruding wall to form a so-called rib, rigidity of the ring-shaped protruding wall can further increase when the cover caps the vessel.

(9) A fitting step overhanging further outward of the ring-shaped concavity formation wall may be formed on the outside of the ring-shaped concavity formation wall of the present invention; and a fitted step fitted into the fitting step and overhanging outward of the ring-shaped protruding wall may be formed on the outside of the ring-shaped protruding wall.

In the preparation jig for a tympanic membrane regenerating agent of the present invention, since the fitted step on the outside of the ring-shaped protruding wall and the fitting step of the ring-shaped concavity formation wall can be fitted together, the vessel and the cover can be fitted together precisely.

(10) A fitting protrusion may be formed on the fitting step of the present invention, and a fitted protrusion fitted onto the fitting protrusion may be formed on the fitted step.

In the preparation jig for a tympanic membrane regenerating agent of the present invention, the vessel and the cover can be fitted together tightly by fitting together the fitting protrusion and the fitted protrusion.

(11) The fitting protrusion and the fitted protrusion of the present invention may be formed at positions where the fitting protrusion and the fitted protrusion are fitted together when the cover is oriented in one orientation around an axial line of the interior space relative to the vessel, and are not fitted together when the cover is oriented in any orientation other than the one orientation.

In the preparation jig for a tympanic membrane regenerating agent of the present invention, the height of the holding portion relative to the vessel can be set by varying the relative orientation of the vessel and the cover.

(12) A preparation vessel for a tympanic membrane regenerating agent of the present invention includes any of the vessel and the holding portion described in any of the above, and a medicinal solution support is housed in advance in a housing portion of the vessel.

The preparation vessel for a tympanic membrane regenerating agent of the present invention has the above operations and functions and can save time and effort for installing a medicinal solution support in a vessel such as a Petri dish to soak the medicinal solution support in a medicinal solution.

(13) An openable pouch enclosing a medicinal solution permeating the medicinal solution support of the present invention may be housed in the interior of the vessel.

In the preparation jig for a tympanic membrane regenerating agent of the present invention, the medicinal solution can be poured easily into the vessel by opening the medicinal solution container, and it is not necessary to weigh or separately prepare the medicinal solution.

Effect of the Invention

A preparation jig for a tympanic membrane regenerating agent and a preparation vessel for a tympanic membrane regenerating agent of the present invention exhibit an effect of enabling convenient preparation of a tympanic membrane regenerating agent by saving time and effort for practitioner's work.

DESCRIPTION OF THE EMBODIMENTS

Figure 1:
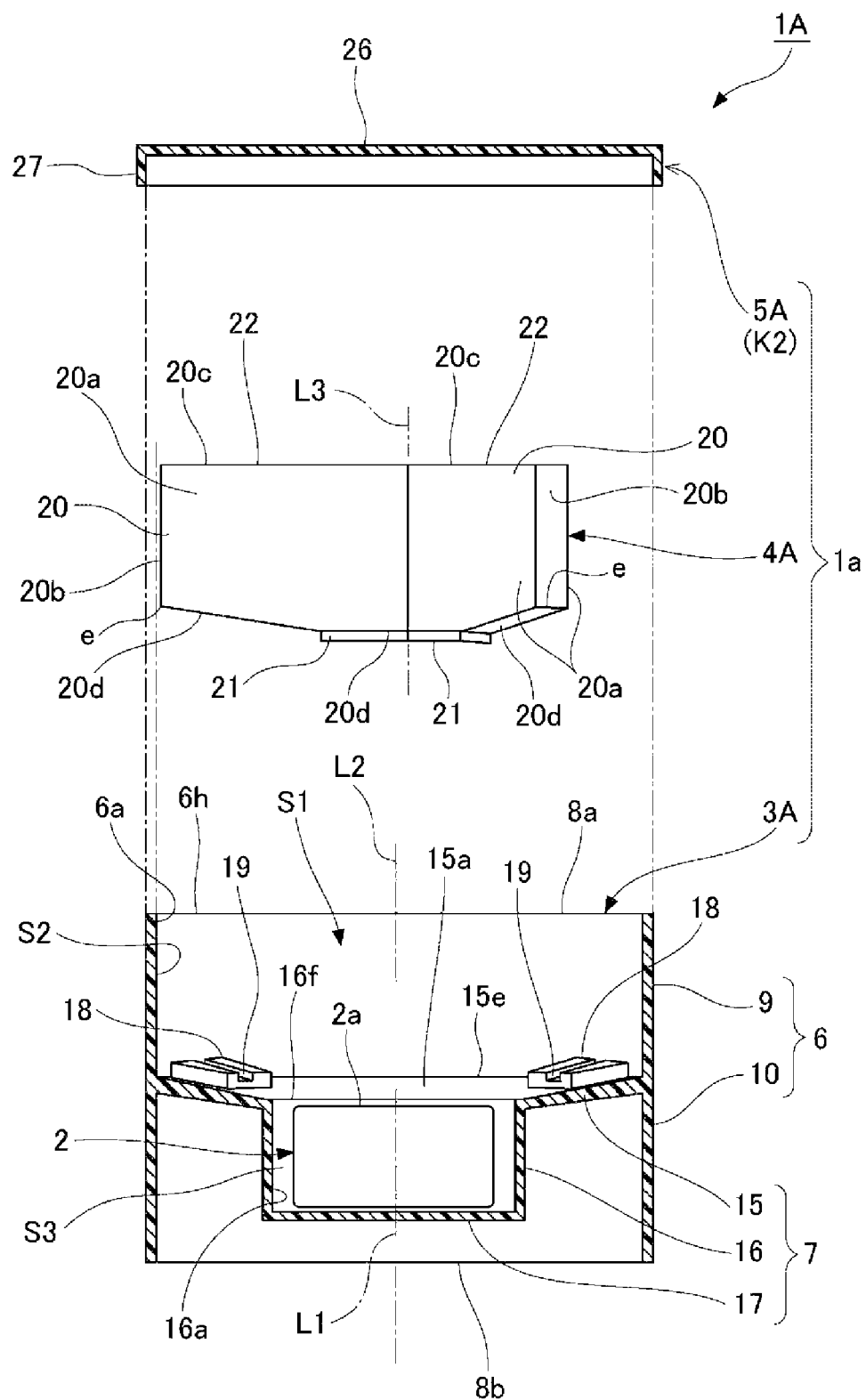
FIG. 1 is a front view illustrating a preparation vessel for a tympanic membrane regenerating agent according to a first embodiment of the present invention being disassembled, and illustrating some parts viewed in cross-section.

Embodiments of a preparation vessel for a tympanic membrane regenerating agent of the present invention and a preparation jig for a tympanic membrane regenerating agent of the present invention will be described below with reference to the drawings. Note that the drawings referenced to in the description below are schematic, and the dimensions and ratios of parts in the drawings may not be identical to the actual dimensions and ratios, and can be changed as appropriate.

As illustrated in FIG. 1, a preparation vessel for a tympanic membrane regenerating agent 1A of a first embodiment includes a medicinal solution support 2 capable of holding a medicinal solution (not illustrated) and a preparation jig for a tympanic membrane regenerating agent 1a.

The preparation jig for a tympanic membrane regenerating agent 1a includes a vessel 3A housing the medicinal solution support 2, a holding member (holding portion) 4A configured to restrict movement of the medicinal solution support 2, and a cover 5A covering the vessel 3A.

Figure 3:
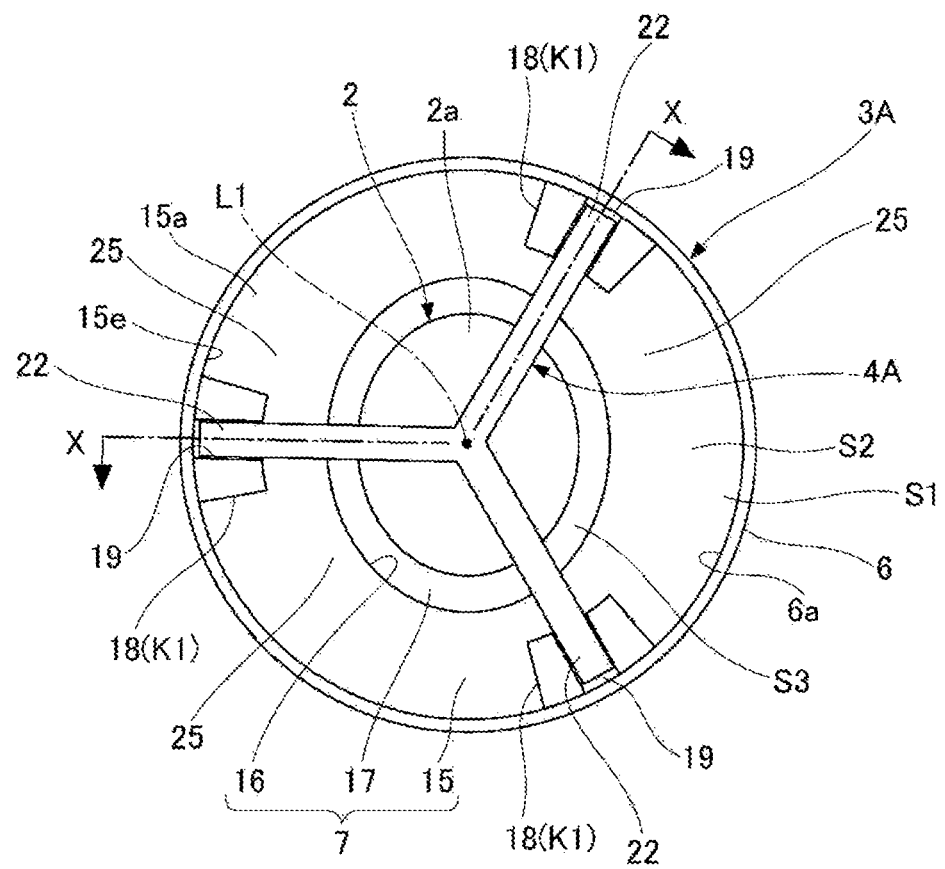
FIG. 3 is a plan view of the preparation vessel for a tympanic membrane regenerating agent according to the first embodiment of the present invention, with a cover of the preparation vessel omitted.

As illustrated in FIGS. 1 and 3, the medicinal solution support 2 is formed in a column shape of which the cross-sectional shape orthogonal to an axial line L1 is an elongated round shape (an oval shape in the present embodiment). A plurality of fine pores are continuously formed in the interior of the medicinal solution support 2, and the interior of the medicinal solution support 2 is in a sponge form.

A material of the medicinal solution support 2 is not limited as long as the material does not hinder a function of the regenerated tympanic membrane, but in the present embodiment, a biodegradable material is favorably used.

Examples of the biodegradable material constituting the medicinal solution support 2 can include gelatin, insoluble collagen, atelocollagen, collagen peptide, elastin and the like. Examples of gelatin include those obtained by, for example, treating bones, ligaments, tendons, skin and the like of cows, pigs, chickens or the like with an acid or alkali to obtain collagen, and heating and extracting the obtained collagen with water. Furthermore, examples of insoluble collagen include those obtained by freeze-drying collagen derived from bones, ligaments, tendons, skin, Achilles tendons and the like of cows, pigs, chickens and the like. The medicinal solution support 2 may include the biodegradable material alone, but may also include other bioabsorbable polymeric materials within the range where the bioabsorbable polymeric materials do not adversely affect characteristics of the biodegradable material. Examples of such bioabsorbable polymeric materials include polylactic acid, polyglycolic acid, and other known materials.

The vessel 3A includes housing walls 6 and 7 forming an interior space S1. The housing walls 6 and 7 include a side wall 6 and a bottom wall 7 overhanging from an inner wall face 6a of the side wall 6.

The side wall 6 has a tubular form and opens in one direction and in a direction opposite to the one direction.

The bottom wall 7 blocks an inner hole of the side wall 6 at a position having a prescribed dimension from one opening edge 8a of the side wall 6, as illustrated in FIG. 1.

A body wall 9 housing a holding member 4A is constituted from the one opening edge 8a of the side wall 6 to a position at which the bottom wall 7 overhangs, and legs 10 enabling the vessel 3A to stand alone are constituted from the position at which the bottom wall 7 overhangs to the other opening edge 8b of the side wall 6.

Note that in the description of each embodiment, the one opening edge 8a side of the vessel 3A is called the upper side, and the other opening edge 8b side (deep side) is called the lower side.

In the interior space S1 of the vessel 3A surrounding the bottom wall 7 and the body wall 9, the upper side constitutes an installation space S2 of the holding member 4A, and the lower side constitutes a housing portion S3 of the medicinal solution support 2.

The bottom wall 7 includes a first bottom portion 15 overhanging at a prescribed dimension from the side wall 6 toward the center of the interior space S1 of the vessel 3A; a second bottom portion 16 extending downward from an inner rim of the first bottom portion 15; and a third bottom portion 17 overhanging from a lower edge of the second bottom portion 16 toward the inside and blocking the second bottom portion 16.

An upper face 15a of the first bottom portion 15 is inclined downward toward an axial line L2 of the side wall 6. Pedestals 18 on which the holding member 4A is mounted are provided on the upper face 15a.

As illustrated in FIG. 1 or FIG. 3, a plurality of (three in the present embodiment) the pedestals 18 are provided along an outer rim 15e of the first bottom portion 15. The plurality of pedestals 18, 18, and 18 are provided to be evenly spaced in the circumferential direction with the axial line L2 as the center. The pedestals 18 are each formed in a substantially trapezoidal shape as seen in plan view at a certain thickness dimension.

A groove 19 indented toward the upper face 15a and extending along the radial direction of the side wall 6 is formed in a center portion in the width direction of each pedestal 18.

A width dimension of the groove 19 is formed to match a thickness dimension P (see FIG. 2) of the holding member 4A fitted into the groove 19.

Figure 4:
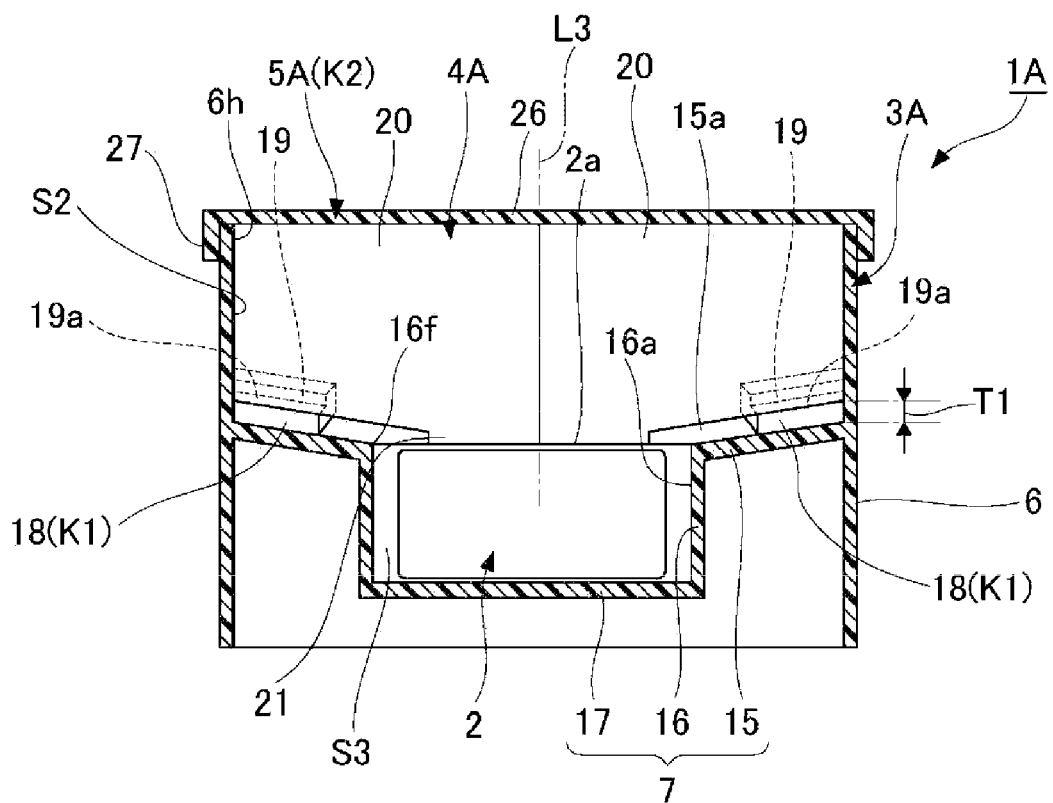
FIG. 4 is a partial longitudinal sectional view along line X-X of the preparation vessel for a tympanic membrane regenerating agent illustrated in FIG. 3, viewed in the directions of the arrows.

As illustrated in FIG. 4, a bottom face 19a of the groove 19 is inclined.

A height dimension T1 from the upper face 15a to the bottom face 19a of the groove 19 is set to match a dimension at which the medicinal solution support 2 disposed in the housing portion S3 is to be compressed.

The pedestal 18 having the above configuration constitutes a lower side locking portion K1 configured to restrict downward movement (toward the housing portion S3 side) of the holding member 4A mounted on the pedestal 18.

As illustrated in FIG. 1, the second bottom portion 16 surrounds the axial line L2 of the side wall 6 in a substantially oval shape as seen in plan view. A dimension in the axial line L2 direction of the second bottom portion 16 is formed to be the same as a dimension in the axial line L1 direction of the medicinal solution support 2.

The third bottom portion 17 is formed in an oval shape as seen in plan view larger than an end face 2a of the medicinal solution support 2.

According to this configuration, the second bottom portion 16 and the third bottom portion 17 form the housing portion S3 configured to house the medicinal solution support 2 and restrict large horizontal movement of the medicinal solution support 2. Furthermore, since the housing portion S3 is formed larger than the medicinal solution support 2, the medicinal solution support 2 can be grasped with tweezers or the like, and can easily be placed in and removed from the housing portion S3.

The cross-sectional area of the inner wall face 6a of the side wall 6 forming the installation space S2 is formed larger than the cross-sectional area of the inner wall face 16a of the second bottom portion 16 forming the housing portion S3.

As illustrated in FIG. 1, the holding member 4A includes a plurality of plate members 22 extending out in a plurality of different directions with an axial line L3 as the center, and is formed detachable from the vessel. The plate members 22 each include a locking plate 20 disposed in the installation space S2 of the vessel 3A, and a depressor 21 configured to be able to enter the housing portion S3 and compress the medicinal solution support 2.

Figure 2:
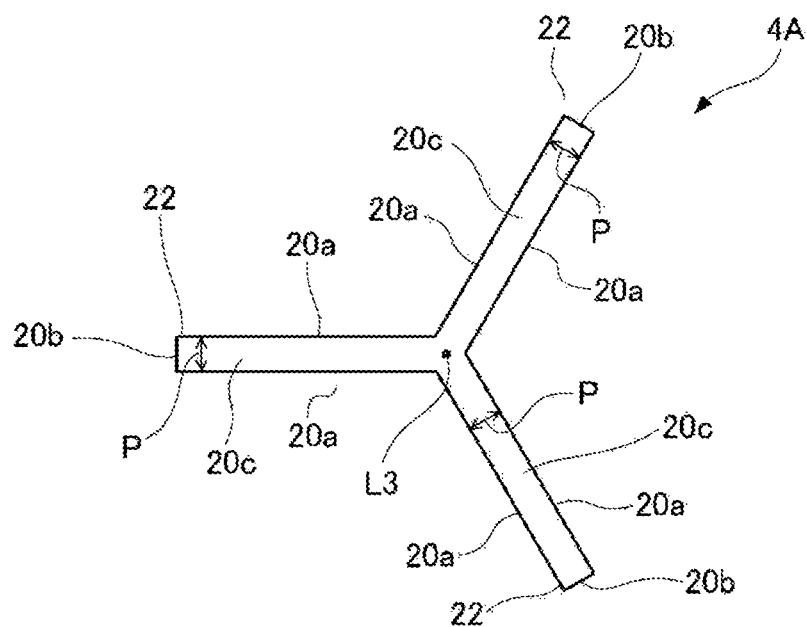
FIG. 2 is a plan view of a holding portion of the preparation vessel for a tympanic membrane regenerating agent according to the first embodiment of the present invention.

As illustrated in FIG. 1 or FIG. 2, the locking plate 20 includes a pair of side plate faces 20a and 20a each forming a substantially trapezoidal shape (precisely, pentagon) and opposing each other, a front end face 20b facing in the extension direction of the locking plate 20, an upper face 20c facing toward the opening 6h side of the vessel 3A, and a lower face 20d opposing the bottom wall 7 side of the vessel 3A.

As illustrated in FIG. 1, an extension dimension from the axial line L3 of the locking plate 20 is set slightly smaller than a dimension from the axial line L2 of the side wall 6 to the inner wall face 6a of the side wall 6, and the locking plate 20 is accommodated exactly in the installation space S2 of the vessel 3A.

The lower face 20d of the locking plate 20 is inclined downward from an edge e of the front end face 20b toward the axial line L3. An angle of inclination of the lower face 20d relative to the horizontal direction is set to match an angle of inclination of the upper face 15a of the first bottom portion 15.

The thickness dimension P of the locking plate 20 is set slightly smaller than the width dimension of the groove 19 of the pedestal 18.

The depressor 21 is formed below the locking plate 20 at an extension dimension smaller than the extension dimension of the locking plate 20. Specifically, the extension dimension of the depressor 21 is smaller than the minimum distance from the axial line L2 of the vessel 3A to the inner wall face 16a of the second bottom portion 16. A thickness dimension of the depressor 21 is the same as the thickness dimension P of the locking plate 20. Thus, the depressor 21 is configured to be able to enter the housing portion S3.

As illustrated in FIG. 4, a protrusion dimension in the axial line L3 direction of the depressor 21 is preferably set in a degree where when the locking plate 20 is mounted in the groove 19 of the pedestal 18, the depressor 21 slightly comes into contact with the end face 2a of the medicinal solution support 2 housed in the housing portion S3.

The holding member 4A is disposed in the installation space S2 with the depressor 21 facing toward the housing portion S3. Then, when the holding member 4A is disposed in the installation space S2 as illustrated in FIG. 3, the holding member 4A is surrounded by the plate members 22 adjacent to each other and the side wall 6, and forms a passage 25 communicating with the housing portion S3.

As illustrated in FIG. 1, the cover 5A includes a top plate 26, and a perimeter plate 27 extending in a ring shape from an outer rim of the top plate 26.

The top plate 26 is formed in a size enabling the top plate 26 to cover entirely the opening 6h of the side wall 6.

The perimeter plate 27 is formed to have an inside diameter slightly larger than an outside diameter of the side wall 6, and is configured to be able to cover the side wall 6 from the outside.

According to this configuration, the cover 5A detachably opens and closes the opening 6h of the side wall 6, and is configured to be firmly affixed to the vessel 3A when the cover 5A is attached to the opening 6h.

Next, a method of preparing a tympanic membrane regenerating agent by using the preparation vessel for a tympanic membrane regenerating agent 1A will be described.

As illustrated in FIGS. 1 and 4, the vessel 3A of the preparation vessel for a tympanic membrane regenerating agent 1A is sealed by the cover 5A in a state where the medicinal solution support 2 is housed in the housing portion S3 of the vessel 3A before use, and the holding member 4A is disposed in the installation space S2.

In this state, since the housing portion S3 of the vessel 3A is formed to match an outer shape of the medicinal solution support 2, unnecessary movement of the medicinal solution support 2 in the housing portion S3 is suppressed, and damage and deformation of the medicinal solution support 2 due to striking of the medicinal solution support 2 against the inner wall face 16a in the vessel 3 are prevented.

Furthermore, the locking plate 20 of the holding member 4A is disposed in the groove 19 of the pedestal 18. In this state, the depressor 21 of the holding member 4A is formed at a protrusion dimension at which the depressor 21 slightly comes into contact with the end face 2a on the upper side of the medicinal solution support 2.

Accordingly, the medicinal solution support 2 is restricted from accidentally moving in the vertical direction in the housing portion S3.

In using this preparation vessel for a tympanic membrane regenerating agent 1A, first, the cover 5A is removed from the vessel 3A to unseal the vessel 3A. The medicinal solution support 2 is disposed in the housing portion S3 of the vessel 3A, and the holding member 4A is disposed in the installation space S2 above the housing portion S3. That is, when the cover 5A is removed, the preparation vessel for a tympanic membrane regenerating agent 1A has already been set in a state where the medicinal solution support 2 is held by the holding member 4A. As a result, a separately prepared medicinal solution can be poured immediately from the opening 6h into the vessel 3A.

The medicinal solution flows directly through the passage 25 illustrated in FIG. 3, or via the side wall 6 or the holding member 4A, onto the bottom wall 7. Since the first bottom portion 15 is inclined downward toward the axial line L2, that is, toward the housing portion S3, the medicinal solution dripping down onto the upper face 15a of the first bottom portion 15 flows to the housing portion S3 together with the medicinal solution dripping down directly from the opening 6h toward the housing portion S3, and is stored.

When a liquid surface of the medicinal solution in the housing portion S3 increases in height, the medicinal solution support 2 disposed in the housing portion S3 floats on the liquid surface due to its buoyancy. However, the end face 2a of the medicinal solution support 2 is held by the holding member 4A to stay below an upper edge 16f of the housing portion S3. The medicinal solution support 2 is gradually soaked in the medicinal solution and absorbs the medicinal solution.

When the housing portion S3 is substantially full of the medicinal solution and stores a sufficient amount of the medicinal solution permeating the medicinal solution support 2, pouring of the medicinal solution is stopped. Here, in a case where the holding member 4A is contrarily pushed upward by the buoyancy of the medicinal solution support 2, the medicinal solution support 2 can be soaked in the medicinal solution by attaching the cover 5A to the opening 6h and affixing the holding member 4A in the installation space S2. In this case, the cover 5A constitutes an upper side locking portion K2 configured to suppress movement of the holding member 4A toward the opening 6h side.

When this state is kept for a while, the medicinal solution permeates entirely the medicinal solution support 2. Subsequently, the cover 5A is removed, and finally, air bubbles remaining in the medicinal solution support 2 are pushed out by pressing the medicinal solution support 2 with tweezers or the like as necessary to cause the medicinal solution to further permeate the medicinal solution support 2, and thus preparation of the tympanic membrane regenerating agent with the medicinal solution held in the medicinal solution support 2 is completed. After the completion of the tympanic membrane regenerating agent, the holding member 4A is removed from the vessel 3A, and then the tympanic membrane regenerating agent can be grasped with tweezers or the like and easily removed from the housing portion S3.

Thus, since the medicinal solution support 2 and the holding member 4A are set in the vessel 3A in advance, the preparation vessel for a tympanic membrane regenerating agent 1A exhibits such an effect that a tympanic membrane regenerating agent can be prepared easily without taking time and effort, but simply by removing the cover 5A, pouring in the medicinal solution from the opening 6h and covering again with the cover 5A.

Furthermore, in the preparation vessel for a tympanic membrane regenerating agent 1A, since the housing portion S3 is formed in consideration of the size of the medicinal solution support 2 and the maneuverability of the medicinal solution support 2, only a necessary amount of the medicinal solution can be put into the housing portion S3 and efficiently permeate the medicinal solution support 2. Accordingly, the preparation vessel for a tympanic membrane regenerating agent 1A exhibits such an effect that the medicinal solution can be used without waste. Furthermore, the preparation vessel for a tympanic membrane regenerating agent 1A exhibits such an effect that since the first bottom portion 15 is inclined downward toward the housing portion S3, when the medicinal solution is poured in or in a case where the medicinal solution overflows the housing portion S3, the medicinal solution can again flow into the housing portion S3 by its own weight.

Furthermore, since the bottom wall 7 of the vessel 3A forms the housing portion S3 to match the shape of the medicinal solution support 2, the area of the third bottom portion 17 is smaller than the cross-sectional area of the side wall 6. However, since the side wall 6 includes the legs 10 extending below the bottom wall 7, there is such an effect that the vessel 3A can stably stand alone.

Note that the holding member 4A is not limited to the configuration described in the present embodiment. The holding member 4A may be formed to incorporate the plate members 22 in any manner, as long as the passage 25 through which the medicinal solution passes is formed as wide as possible, and the holding member 4A can suitably suppress the medicinal solution support 2 in the housing portion S3.

Specifically, the holding member 4A may include the plate members 22 dividing a circumference with the axial line L3 as the center into four or more equal parts. Alternatively, the holding member 4A may be formed to incorporate the plate members 22 in a lattice form. In this case, the holding member 4A is configured such that at least parts of the plate members 22 are located on the housing portion S3. The holding member 4A is more preferably configured such that at least one intersection is located on the housing portion S3.

Furthermore, the passage 25 may be formed in a groove shape extending vertically in the inner wall face 6a of the side wall 6.

The preparation vessel for a tympanic membrane regenerating agent 1A also exhibits similar operations, functions and effects to the operations, functions and effects of the present embodiment by using the holding member 4A described above.

Figure 5:
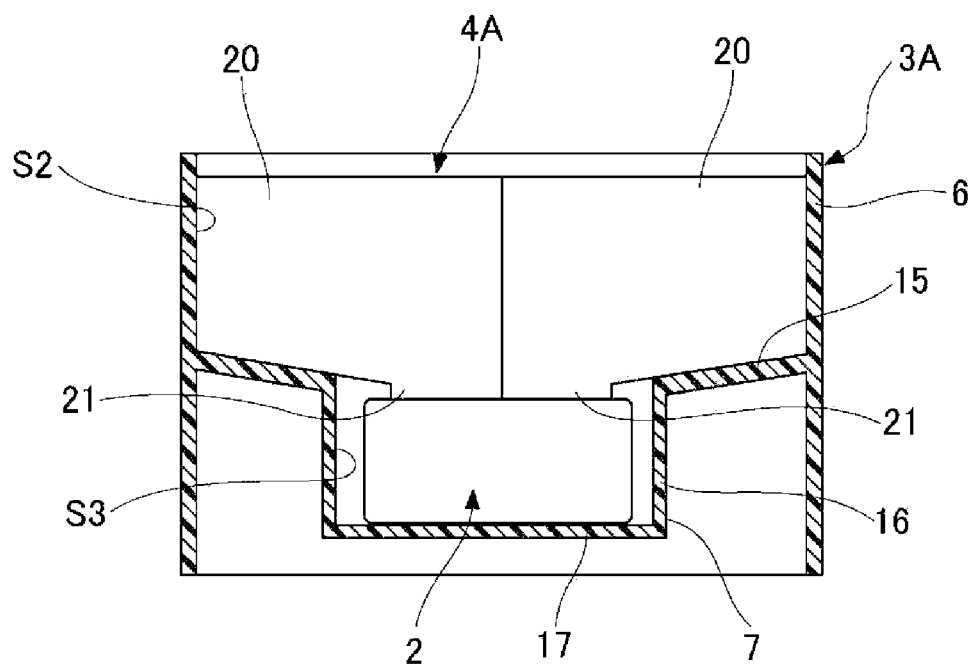
FIG. 5 is a partial longitudinal sectional view illustrating a method of use of the preparation vessel for a tympanic membrane regenerating agent according to the first embodiment of the present invention.

Furthermore, as illustrated in FIG. 4, air remaining in the medicinal solution support 2 after the medicinal solution has permeated the medicinal solution support 2 may be expelled by removing the holding member 4A from the pedestal 18, positioning the locking plate 20 on the first bottom portion 15 between the pedestals 18 and 18 as illustrated in FIG. 5, causing the depressor 21 to enter the housing portion S3, and compressing the medicinal solution support 2.

Figure 6:
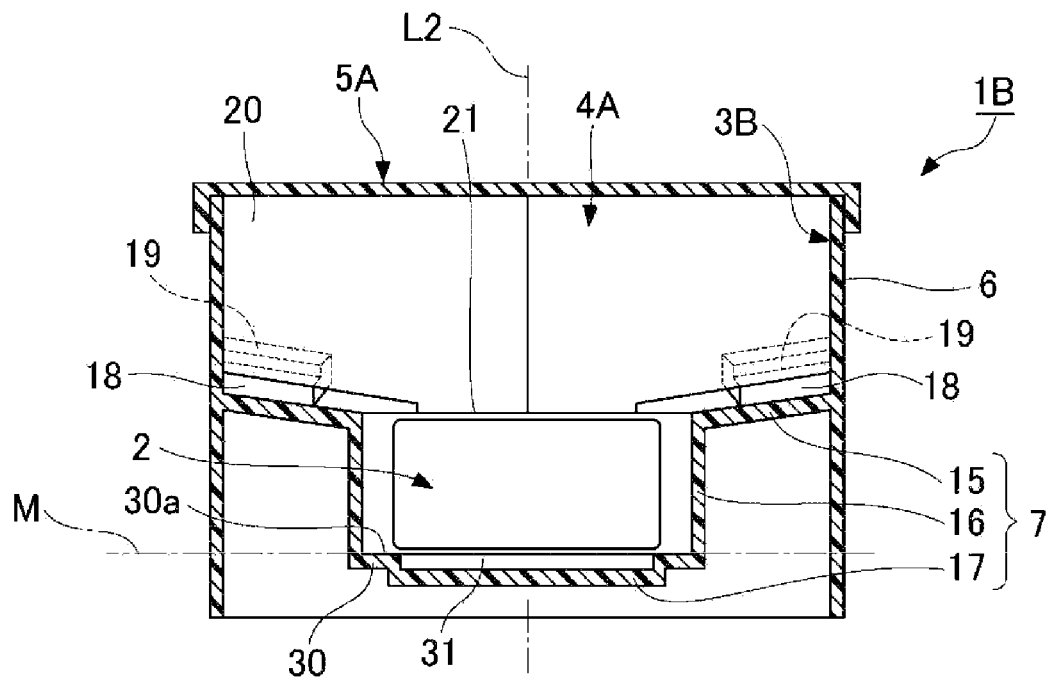
FIG. 6 is a partial longitudinal sectional view illustrating a preparation vessel for a tympanic membrane regenerating agent according to a second embodiment of the present invention.

Next, a second embodiment of the present invention will be described with reference to FIG. 6. As for the embodiment described here, elements including configurations differing from those in the first embodiment will mainly be described. Elements including the same configurations as those in the first embodiment are given the same reference signs, and description of those elements will be omitted. The same applies to the third embodiment and thereafter.

A preparation vessel for a tympanic membrane regenerating agent 1B of the present embodiment differs from the vessel 3A of the preparation vessel for a tympanic membrane regenerating agent 1A mainly in a shape of a vessel 3B. The vessel 3B of the preparation vessel for a tympanic membrane regenerating agent 1B includes a mounting portion 30 configured to mount a medicinal solution support 2 on a third bottom portion 17, and a reservoir 31 of a medicinal solution formed on the inside of the mounting portion 30.

The mounting portion 30 is formed with a ring-shaped step formed at a prescribed width dimension along an inner rim of the third bottom portion 17. An upper face 30a of the mounting portion 30 is formed on a plane M orthogonal to an axial line L2 toward the inside.

The reservoir 31 is a space formed on the inside of the mounting portion 30 by being indented downward from the mounting portion 30.

In the preparation vessel for a tympanic membrane regenerating agent 1B, the medicinal solution support 2 is disposed on the mounting portion 30 and the reservoir 31 can house a medicinal solution. Accordingly, the preparation vessel for a tympanic membrane regenerating agent 1B exhibits such an effect that when the medicinal solution flows into a housing portion S3, the medicinal solution is stored below the medicinal solution support 2, and as a result, the medicinal solution can also permeate from below the medicinal solution support 2 and can be absorbed more quickly.

Figure 7:
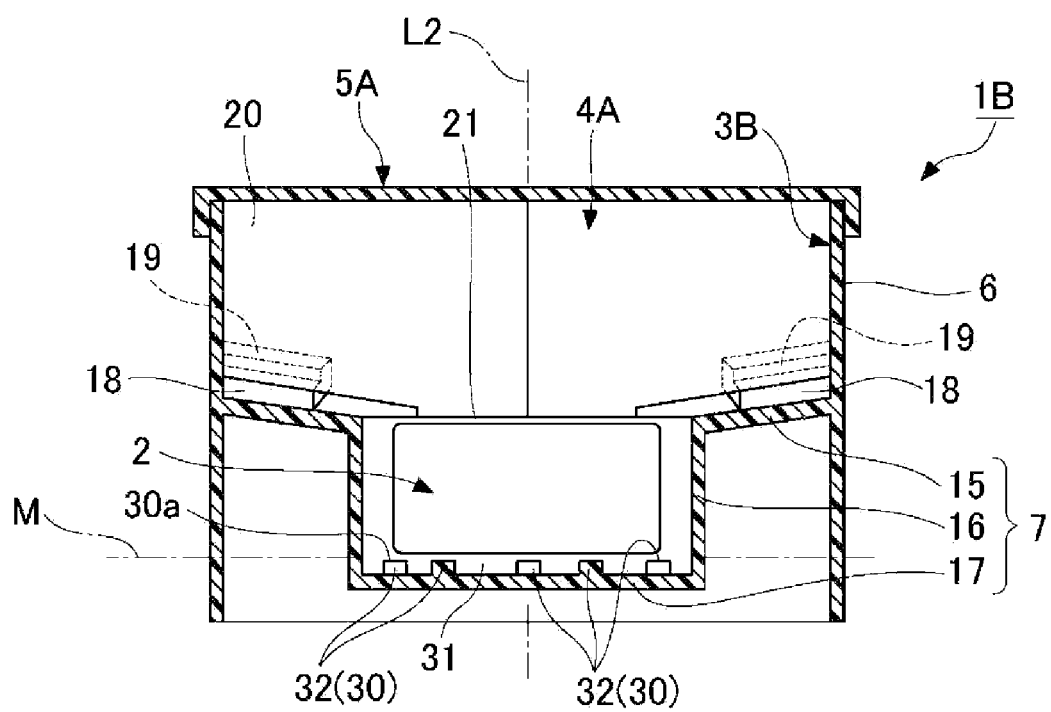
FIG. 7 is a partial longitudinal sectional view illustrating a modification example of the preparation vessel for a tympanic membrane regenerating agent according to the second embodiment of the present invention.

Note that the reservoir 31 of the preparation vessel for a tympanic membrane regenerating agent 1B can be formed in any manner as long as a space for storing the medicinal solution below the medicinal solution support 2 is formed. Specifically, as illustrated in FIG. 7, the mounting portion 30 may be formed with a plurality of protrusions 32, 32 . . . separated from one another, and the reservoir 31 may be formed between the protrusions 32.

Figure 8:
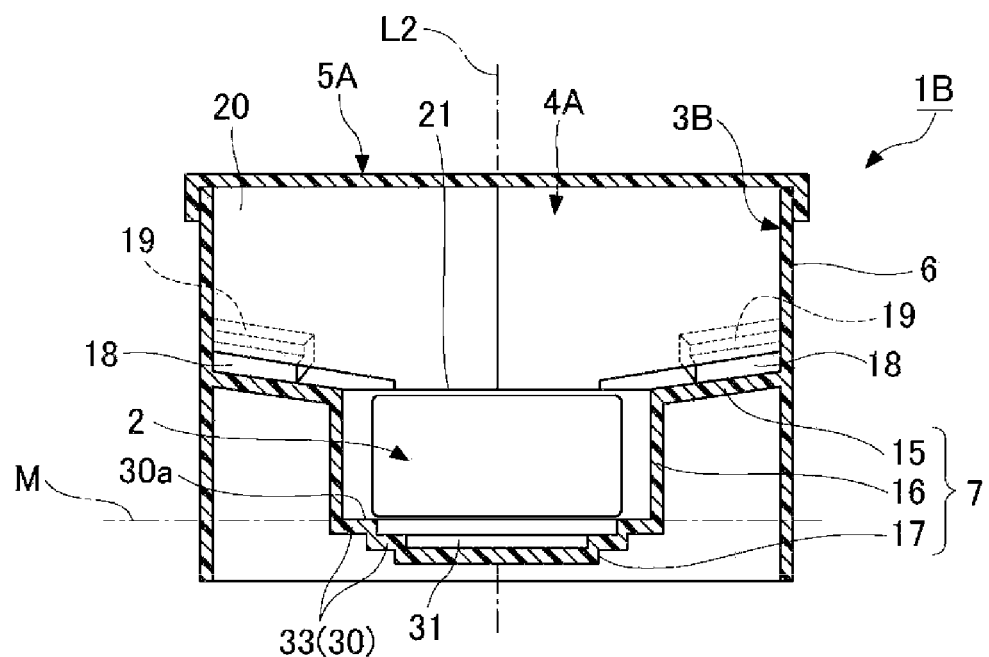
FIG. 8 is a partial longitudinal sectional view illustrating a modification example of the preparation vessel for a tympanic membrane regenerating agent according to the second embodiment of the present invention.

Furthermore, as illustrated in FIG. 8, the mounting portion 30 may include a plurality of steps 33, 33 . . . becoming smaller in diameter and deeper toward below in the axial line L2 direction. When the mounting portion 30 is configured in this manner, there is such an effect that the medicinal solution support 2 having different cross-sectional area is easily accommodated. Furthermore, the reservoir 31 is always formed below the mounting portion 30. Accordingly, when the medicinal solution support 2 is mounted on the mounting portion 30, there is such an effect that the medicinal solution can efficiently permeate from below the medicinal solution support 2.

Figure 9:
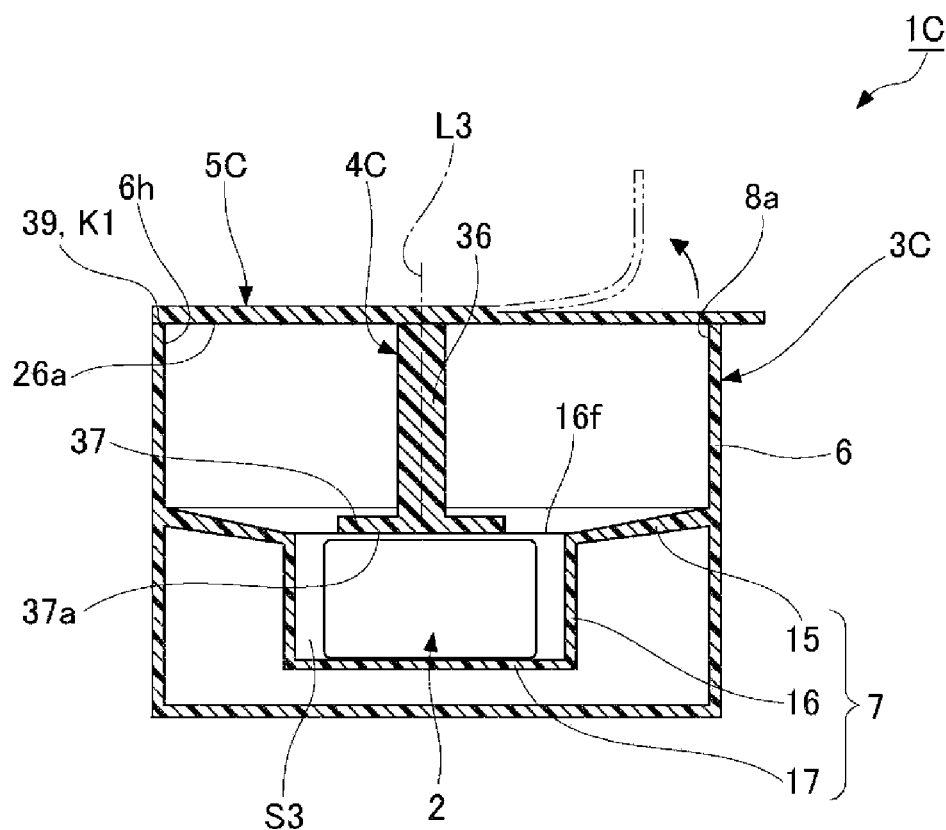
FIG. 9 is a partial longitudinal sectional view illustrating a preparation vessel for a tympanic membrane regenerating agent according to a third embodiment of the present invention.

Next, a third embodiment of the present invention will be described with reference to FIG. 9.

In a preparation vessel for a tympanic membrane regenerating agent 1C of the third embodiment, a holding member 4C is affixed at the center of a lower face 26a of a cover 5C having flexibility and a plate-like shape.

The holding member 4C includes a column-shaped locking portion 36 and a disk-shaped depressor 37.

A lower face 37a of the depressor 37 is formed substantially level, with area smaller than area of a housing portion S3.

A length dimension in the axial line L3 direction of the holding member 4C is set such that the holding member 4C is positioned at an upper edge 16f of the housing portion S3 in a state where an opening 6h of the vessel 3C is blocked by the cover 5C.

When the cover 5C is disposed on the opening 6h, the depressor 37 is affixed to the cover 5C to be positioned above a medicinal solution support 2 disposed in the housing portion S3. Furthermore, the lower face 37a of the depressor 37 is affixed to be positioned slightly in contact with the medicinal solution support 2.

The cover 5C is manually and removably bonded by using an adhesive or the like to an upper end face 39 of the vessel 3C, and seals the vessel 3C. Note that since the holding member 4C is affixed to the cover 5C and the cover 5C is bonded to the upper end face 39 of the vessel 3C, a pedestal 18 configured to mount the holding member 4C on a bottom wall 7 is not formed.

In the present embodiment, the upper end face 39 of the vessel 3C supporting the cover 5C constitutes a lower side locking portion K1 of the holding member 4C.

According to the above configuration, the medicinal solution support 2 housed in the housing portion S3 is restricted from accidentally moving in the vertical direction.

In using the preparation vessel for a tympanic membrane regenerating agent 1C, the cover 5C is stripped off such that the opening 6h is unsealed to a degree of not more than half-way, that is, to a degree where the holding member 4C affixed to the cover 5C does not accidentally move, and a medicinal solution is poured in.

The preparation vessel for a tympanic membrane regenerating agent 1C is left for a while in this state or after the opening 6h is reclosed, and the cover 5C is entirely peeled off from the vessel 3C at the time when the medicinal solution has permeated the medicinal solution support 2. Then, air remaining in the medicinal solution support 2 is expelled by the holding member 4C or the like as necessary, and preparation of a tympanic membrane regenerating agent is completed.

Similar operations, functions and effects as those of the preparation vessel for a tympanic membrane regenerating agent 1A of the first embodiment are also obtained by this preparation vessel for a tympanic membrane regenerating agent 1C.

Figure 10:
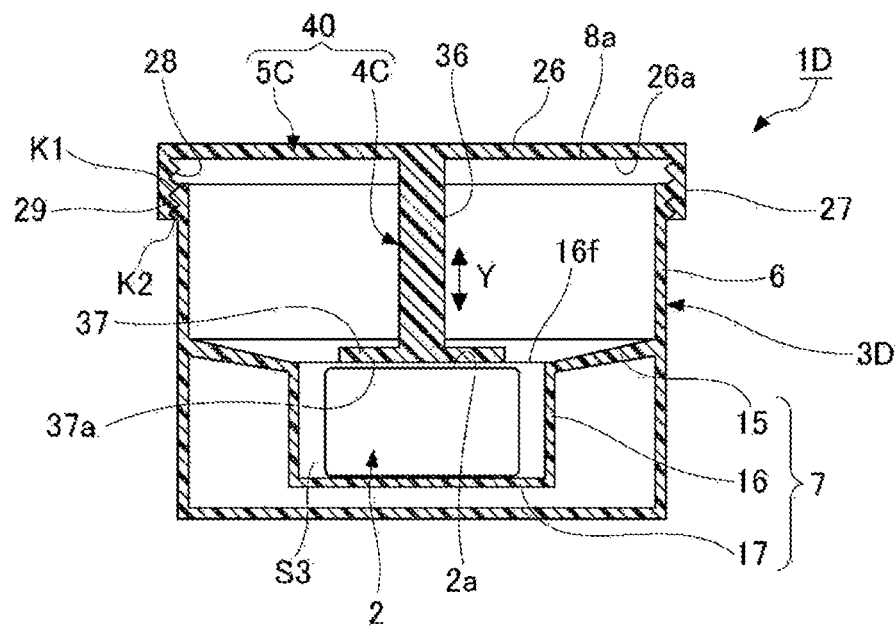
FIG. 10 is a partial longitudinal sectional view illustrating a modification example of the preparation vessel for a tympanic membrane regenerating agent according to the third embodiment of the present invention.

Note that instead of the cover 5C and the holding member 4C described in the present embodiment, a combination holding portion-cover 40 being obtained by integrally forming the cover 5C and the holding member 4C with the same resin material and being capable of serving as both the cover 5C and the holding member 4C may be used as illustrated in FIG. 10.

In this modification example, the combination holding portion-cover 40 includes a top plate 26, a holding member 4C protruding from a lower face 26a of the top plate 26, and a perimeter plate 27 extending in the axial line L4 direction from an outer rim of the top plate 26.

As with the holding member 4C described above, the holding member 4C includes a column-shaped locking portion 36 and a disk-shaped depressor 37.

A female screw portion 28 is formed on an inner circumferential face of the perimeter plate 27.

On an outer circumferential face of a side wall 6 of a vessel 3D, a male screw portion 29 is formed at a portion corresponding to the female screw portion 28 when the cover 5C is attached.

The combination holding portion-cover 40 of the present modification example is positioned, for example, such that when the combination holding portion-cover 40 is attached to the vessel 3D and screwed onto the vessel 3D with about a half turn, the lower face 37a of the depressor 37 slightly comes into contact with an end face 2a of the medicinal solution support 2, and the end face 2a of the medicinal solution support 2 can be depressed gradually as the combination holding portion-cover 40 is screwed onto the vessel 3D more deeply.

In a preparation vessel for a tympanic membrane regenerating agent 1D of the present modification example, the combination holding portion-cover 40 is shallowly screwed onto the vessel 3D for a while after the medicinal solution is poured into the housing portion S3. Then, at the time when the medicinal solution permeates the medicinal solution support 2 to a certain extent, the combination holding portion-cover 40 is further screwed onto the vessel 3D, and air bubbles contained in the medicinal solution support 2 are removed by holding the medicinal solution support 2. Then, the combination holding portion-cover 40 is again shallowly screwed onto the vessel 3D.

In this configuration, a face of the vessel 3D facing toward the upper side of the male screw portion 29 constitutes a lower side locking portion K1 configured to restrict downward movement of the combination holding portion-cover 40. Furthermore, a face facing toward the lower side of the male screw portion 29 constitutes an upper side locking portion K2 configured to restrict upward movement of the combination holding portion-cover 40.

Thus, in the preparation vessel for a tympanic membrane regenerating agent 1D of the present modification example, after the combination holding portion-cover 40 is removed and the medicinal solution is poured in, movement of the holding member 4C and consequently movement of the medicinal solution support 2 are restricted or the medicinal solution support 2 is compressed or restored to make the medicinal solution permeate by adjusting the degree of screwing of the combination holding portion-cover 40.

Accordingly, there is such an effect that the medicinal solution can more easily permeate the medicinal solution support 2 as uniformly as possible.

Figure 11:
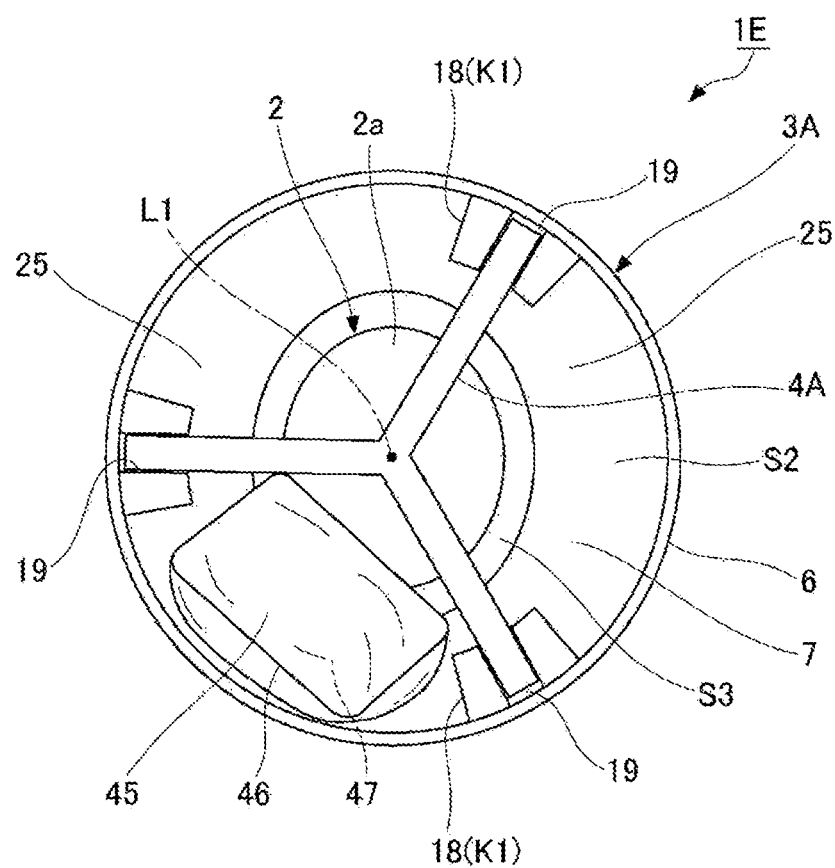
FIG. 11 is a plan view of a preparation vessel for a tympanic membrane regenerating agent according to a fourth embodiment of the present invention, with a cover of the preparation vessel omitted.

Next, a fourth embodiment of the present invention will be described with reference to FIG. 11.

A preparation vessel for a tympanic membrane regenerating agent 1E of the fourth embodiment includes a medicinal solution container (pouch) 45 in a gap located between a holding member 4A and a vessel 3A and formed in an installation space S2.

The medicinal solution container 45 includes a resin film 46 and a medicinal solution 47. The resin film 46 is formed into a pouch shape with a material easy to open by using a tool or the like. The medicinal solution 47 is sealed inside the resin film 46.

In using the preparation vessel for a tympanic membrane regenerating agent 1E, a cover 5A illustrated in FIG. 1 is removed from the vessel 3A, and then the medicinal solution container 45 is opened. Examples of an opening method include a method including cutting the resin film 46 constituting the medicinal solution container 45 by using a sharp tool (not illustrated), and a method including opening an unsealing portion (not illustrated) formed in advance on a portion of the medicinal solution container 45. When the medicinal solution container 45 is opened and the medicinal solution 47 inside the medicinal solution container 45 flows from the resin film 46, the medicinal solution 47 flows down through a passage 25 onto a bottom wall 7. Subsequently, a tympanic membrane regenerating agent is prepared in the same manner as in the preparation vessel for a tympanic membrane regenerating agent 1A.

Next, a preparation vessel for a tympanic membrane regenerating agent 1F of a fifth embodiment of the present invention will be described with reference to FIGS. 12 to 14.

Figure 12:
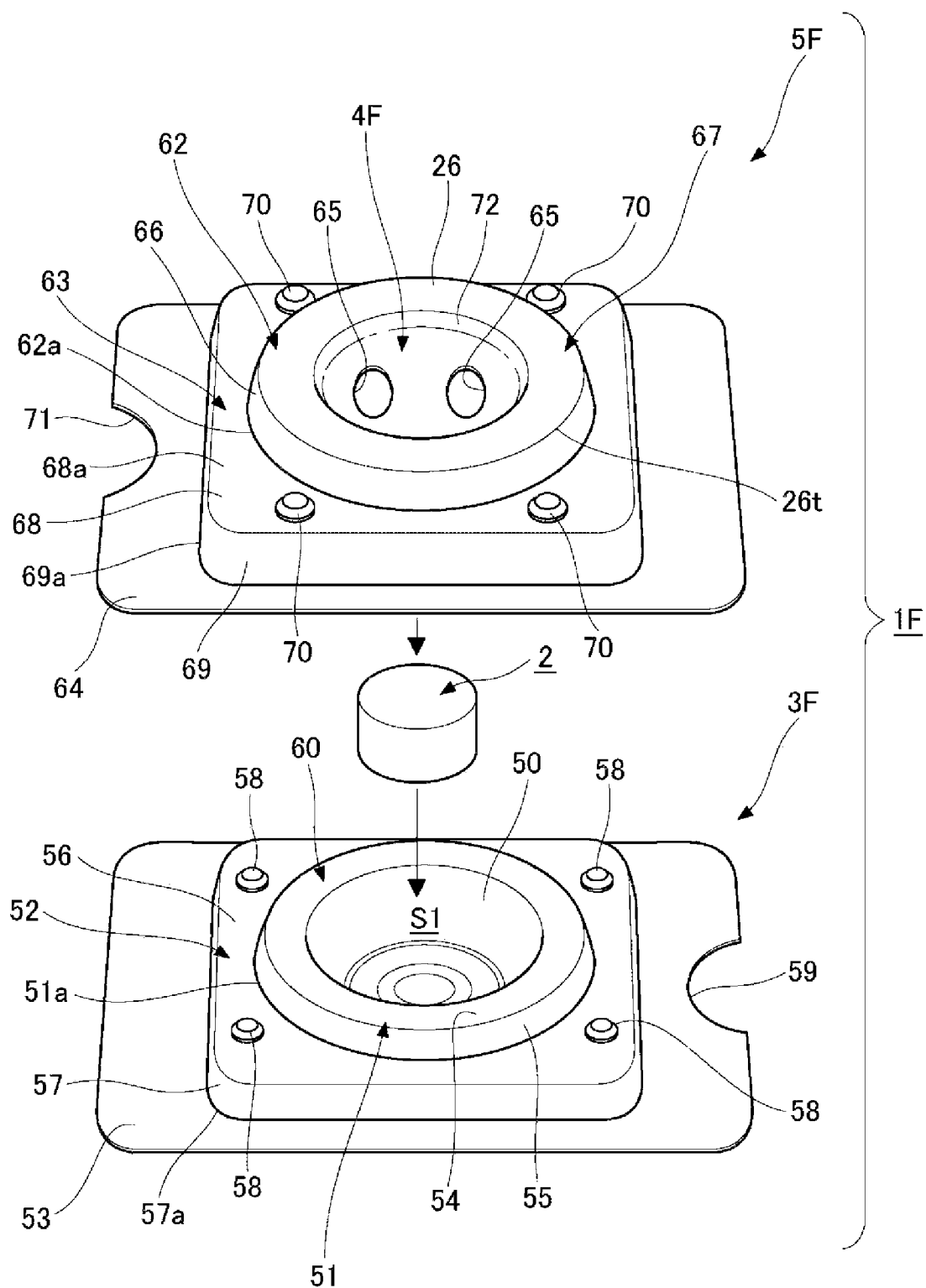
FIG. 12 is a perspective view illustrating a preparation vessel for a tympanic membrane regenerating agent according to a fifth embodiment of the present invention being disassembled.

As illustrated in FIG. 12, the preparation vessel for a tympanic membrane regenerating agent 1F includes a vessel 3F formed with indentations and protrusions provided on a film-like member, and a cover 5F on which indentations and protrusions fitted into the indentations and protrusions of the vessel 3F are formed.

The vessel 3F includes a housing wall 50 forming an interior space S1; a ring-shaped protruding wall 51 surrounding the interior space S1 on the outside of the housing wall 50 and protruding toward the opening side; a fitted step 52 overhanging outward of the ring-shaped protruding wall 51; and a flange 53 overhanging outward of the fitted step 52.

The ring-shaped protruding wall 51 includes a first top face 54 overhanging horizontally from a top edge of the housing wall 50, and a first inclined face 55 inclining downward from the first top face 54.

The fitted step 52 overhangs in a square shape as seen in plan view toward the outside from a lower edge 51a of the ring-shaped protruding wall 51. The fitted step 52 includes a second top face 56, and a second inclined face 57 facing downward from an outer rim of the second top face 56.

On the second top face 56 of the fitted step 52, four fitted protrusions 58 each having a circular shape as seen in plan view and protruding upward are formed near corners.

The fitted protrusions 58 are formed at positions corresponding to corners of an imaginary rectangle.

Further, a flange 53 is formed overhanging from a lower edge 57a of the second inclined face 57 horizontally in a rectangular shape as seen in plan view.

The flange 53 is formed in a rectangular shape as seen in plan view. A semicircular notch 59 is formed on one of a pair of short sides forming the flange 53.

According to the above configuration, the fitted step 52 has a shape in which the fitted step 52 swells from the flange 53. Furthermore, the ring-shaped protruding wall 51 has a shape in which the ring-shaped protruding wall 51 swells in a ring shape from the second top face 56 of the fitted step 52, and forms a first projection 60 projecting in a ring shape together with the housing wall 50.

Figure 13A:
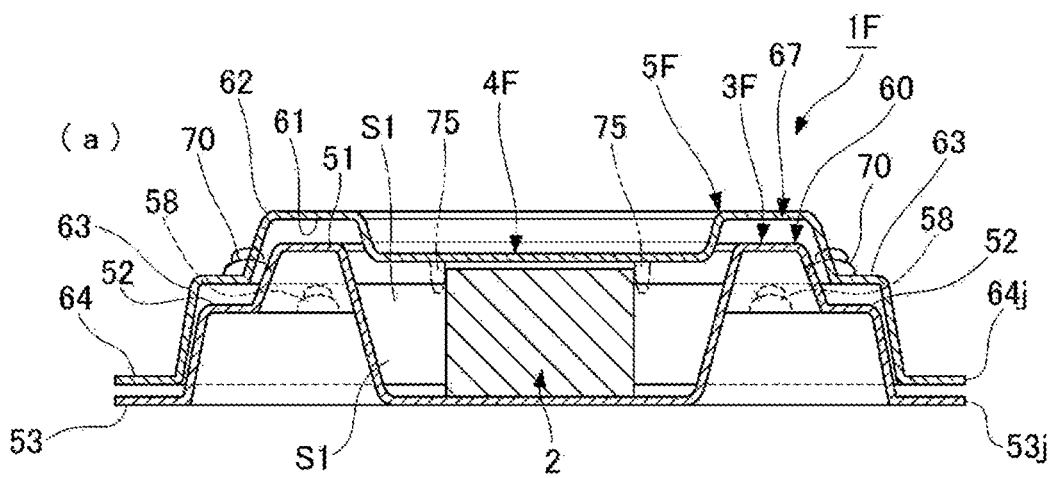
FIG. 13A is a cross-sectional view along line X-X of the preparation vessel for a tympanic membrane regenerating agent according to the fifth embodiment illustrated in FIG. 13B, viewed in the directions of the arrows.

The cover 5F includes a holding portion 4F including a concavity indented toward the inside of the top plate 26; a ring-shaped concavity formation wall 62 forming a ring-shaped concavity 61 illustrated in FIG. 13A on the lower face side of the top plate 26 on the outside of the holding portion 4F; a fitting step 63 overhanging in a rectangular shape as seen in plan view outward of the ring-shaped concavity formation wall 62; and a flange 64 overhanging from the fitting step 63.

The holding portion 4F is formed with a concavity in which the top plate 26 is indented on the inside at a prescribed dimension from an outer rim 26t along the outer rim 26t of the top plate 26. Two through-holes 65 through which the medicinal solution passes are formed in the holding portion 4F, and spaced from each other in the radial direction. The through-holes 65 constitute a passage 25 of the medicinal solution.

The ring-shaped concavity formation wall 62 includes a ring-shaped outer circumferential portion of the top plate 26, and a first inclined wall 66 standing in a ring shape diagonally downward from the outer rim 26t of the top plate 26.

The ring-shaped concavity formation wall 62 and an inclined face 72 of the holding portion 4F form a second projection 67 projecting in a ring shape on the fitting step 63.

The fitting step 63 includes a horizontal wall 68 overhanging in a square shape as seen in plan view outward from a lower edge 62a of the ring-shaped concavity formation wall 62, and a second inclined wall 69 standing to incline downward from an outer rim of the horizontal wall 68.

Fitting protrusions 70 fitted into the fitted protrusions 58 of the vessel 3F are formed on an upper face 68a of the horizontal wall 68. Four fitting protrusions 70 are formed at positions corresponding to corners of an imaginary rectangle near four corners of the horizontal wall 68. The fitted protrusions 58 each have a size slightly smaller than a size of each fitting protrusion 70.

A flange 64 is formed overhanging from a lower edge 69a of the second inclined wall 69 horizontally in a rectangular shape as seen in plan view.

The flange 64 is formed in a substantially rectangular shape as seen in plan view. A semicircular notch 71 is formed on one of a pair of short sides forming the flange 64.

According to the above configuration, the first projection 60 is formed in a shape slightly smaller than and similar to a shape of the second projection 67, and the second projection 67 is fitted onto the first projection 60.

The fitted step 52 is formed in a shape slightly smaller than and similar to a shape of the fitting step 63, and the fitting step 63 is easily fitted onto the fitted step 52.

Figure 13B:
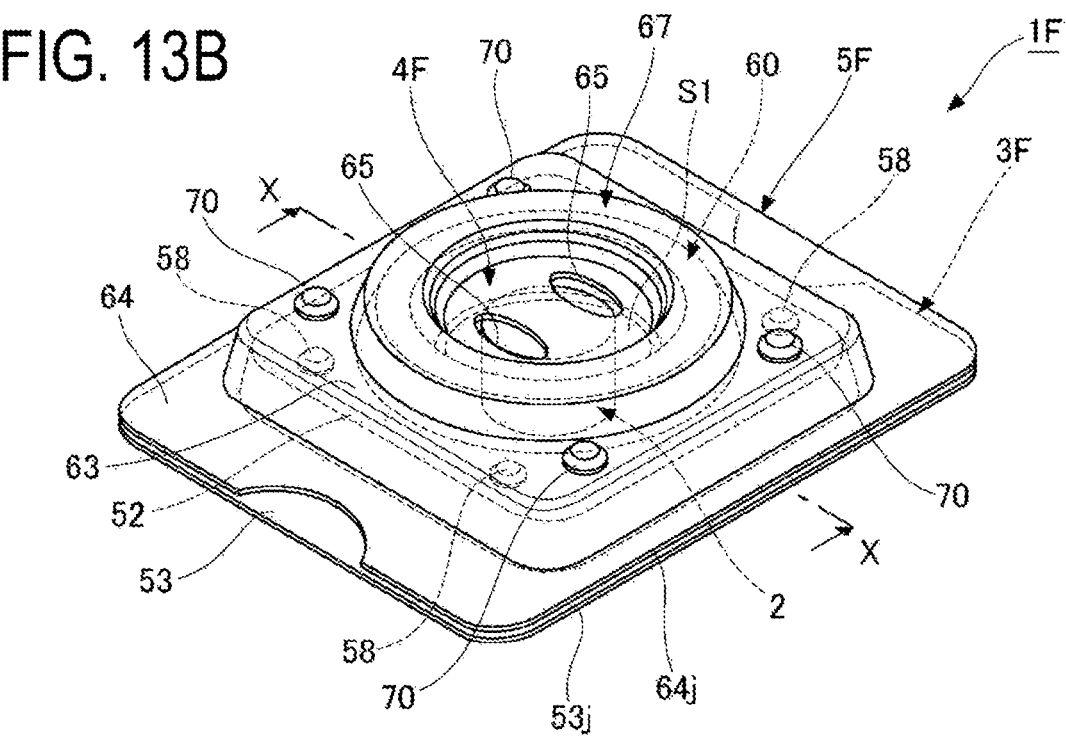
FIG. 13B is a perspective view of the preparation vessel for a tympanic membrane regenerating agent according to the fifth embodiment of the present invention.

As illustrated in FIGS. 13A and 13B, when the cover 5F and the vessel 3F are overlaid with respective long edges 64j and 53j of the flange 64 of the cover 5F and the flange 53 of the vessel 3F aligned to each other, the first projection 60 and the second projection 67 are fitted together, and the fitted step 52 and the fitting step 63 are fitted together. In this case, however, the fitted protrusions 58 and the fitting protrusions 70 are not aligned to one another, and are not fitted together.

Figure 14A:
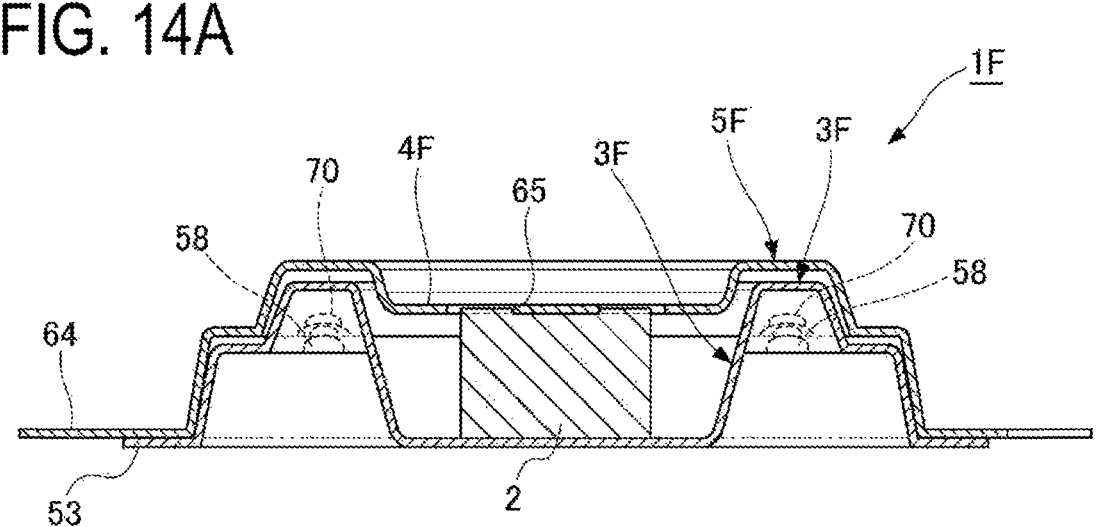
FIG. 14A is a cross-sectional view along line Y-Y of the preparation vessel for a tympanic membrane regenerating agent according to the fifth embodiment illustrated in FIG. 14B, viewed in the directions of the arrows.
Figure 14B:
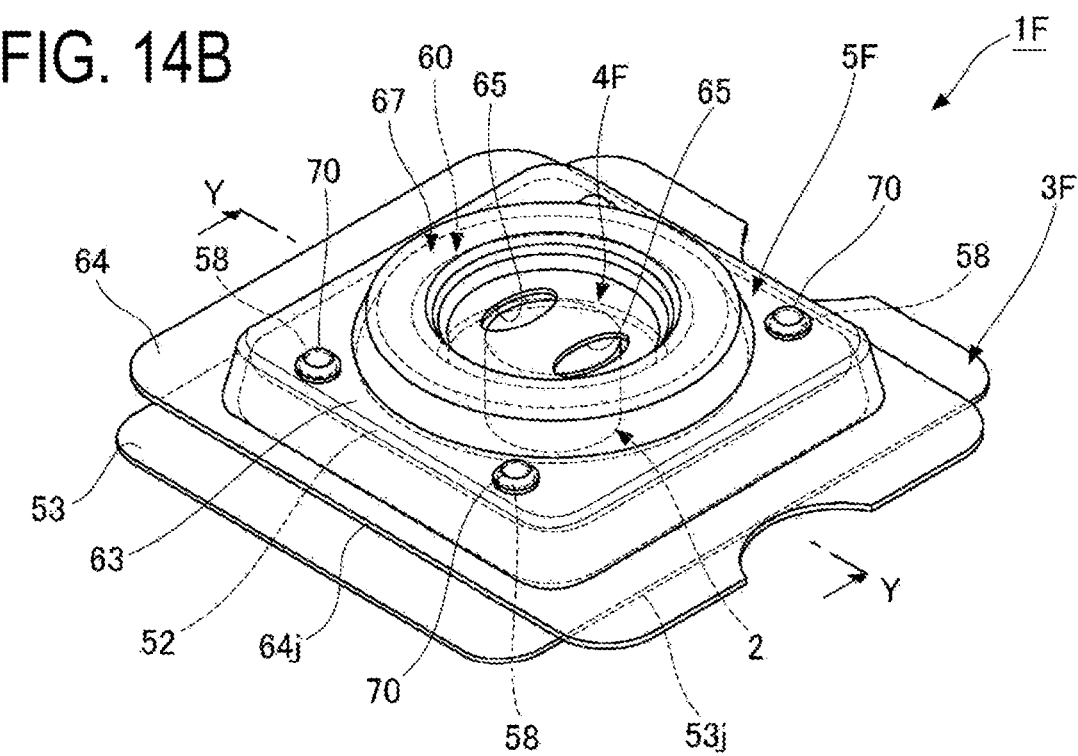
FIG. 14B is a perspective view of the preparation vessel for a tympanic membrane regenerating agent according to the fifth embodiment of the present invention.

On the other hand, as illustrated in FIGS. 14A and 14B, when the cover 5F is overlaid on the vessel 3F with the orientation rotated around an axial line L2 of an interior space S1 by 90 degrees such that the respective long edges 64j and 53j of the flange 64 of the cover 5F and the flange 53 of the vessel 3F are orthogonal to each other, the first projection 60 and the second projection 67 are fitted together, the fitted step 52 and the fitting step 63 are fitted together, and the fitted protrusions 58 and the fitting protrusions 70 are fitted together.

Next, a method of use of the preparation vessel for a tympanic membrane regenerating agent 1F of the present embodiment will be described.

Before use, as illustrated in FIGS. 13A and 13B, the cover 5F covers the vessel 3F in a state where the medicinal solution support 2 is disposed in the interior space S1 of the vessel 3F.

Then, when the medicinal solution drips down into the holding portion 4F, the medicinal solution passes through the through-holes 65 and gradually fills the interior space S1 of the vessel 3F. At this time, since the second projection 67 protrudes on a periphery of the holding portion 4F, a prescribed amount of the medicinal solution is accumulated inside the second projection 67.

In this state, since the long edge 64j of the flange 64 is disposed in parallel to the long edge 53j of the flange 53 of the vessel 3F, the fitted protrusions 58 are not fitted into the fitting protrusions 70. Accordingly, the cover 5F floats above the vessel 3F by an amount of protrusion of the fitted protrusions 58 relative to the vessel 3F.

When the medicinal solution support 2 becomes completely soaked in the medicinal solution in the interior space S1, the medicinal solution gradually permeates the medicinal solution support 2, and the medicinal solution support 2 becomes soft.

Then, as illustrated in FIGS. 14A and 14B, the orientation of the flange 64 of the cover 5F is rotated by 90 degrees, to dispose the long edge 64j of the flange 64 orthogonal to the long edge 53j of the flange 53 of the vessel 3F.

When the orientation of the cover 5F is changed in this manner, the fitting protrusions 70 face the fitted protrusions 58. Then, when the fitting protrusions 70 are fitted onto the fitted protrusions 58, the holding portion 4F enters the interior space S1 and compresses the medicinal solution support 2, and the medicinal solution can further permeate the medicinal solution support 2.

When this state is kept for a while, the medicinal solution permeates the medicinal solution support 2 substantially completely, and thus the cover 5F is removed to obtain a tympanic membrane regenerating agent.

As illustrated in FIG. 12, since the ring-shaped protruding wall 51 is formed outside the housing wall 50, the fitted step 52 is further formed outside the ring-shaped protruding wall 51, and the flange 53 is further formed, the vessel 3F of the preparation vessel for a tympanic membrane regenerating agent 1F described above is generally formed flat, and thus is mounted stably.

Furthermore, the cover 5F covering the vessel 3F is formed flat in substantially the same shape as the shape of the vessel 3F such that the cover 5F can also be fitted onto the vessel 3F.

Accordingly, there is such an effect that the preparation vessel for a tympanic membrane regenerating agent 1F can be mounted stably.

Furthermore, the preparation vessel for a tympanic membrane regenerating agent 1F exhibits such an effect that since the ring-shaped protruding wall 51 is provided on the outside of the housing wall 50 of the vessel 3F, rigidity of the housing wall 50 can increase. Furthermore, the preparation vessel for a tympanic membrane regenerating agent 1F exhibits such an effect that even when external force is applied to the vessel 3F, deformation of the housing wall 50 due to the applied external force can be prevented by the ring-shaped protruding wall 51 that receives the external force.

The cover 5F includes the ring-shaped concavity formation wall 62 corresponding to the ring-shaped protruding wall 51, and exhibits such an effect that when the cover 5F caps the vessel 3F, rigidity of the ring-shaped protruding wall 51 can further increase.

Furthermore, in the preparation vessel for a tympanic membrane regenerating agent 1F, since the fitted step 52 on the outside of the ring-shaped protruding wall 51 and the fitting step 63 of the ring-shaped concavity formation wall 62 are fitted together, the vessel 3F and the cover 5F can also be fitted together precisely by the fitting of the fitted step 52 and the fitting step 63.

Furthermore, the fitted protrusions 58 are formed on the second top face 56 of the fitted step 52 located close to the first top face 54, and the fitting protrusions 70 are formed on the upper face 68a of the fitting step 63 located close to the top plate 26. Accordingly, the preparation vessel for a tympanic membrane regenerating agent 1F exhibits such an effect that the cover 5F can be affixed easily on the vessel 3F by fitting the fitted protrusions 58 and the fitting protrusions 70 together.

Furthermore, since the vessel 3F and the cover 5F can be integrally molded by embossing or vacuum drawing or the like with use of a single sheet of resin film material for each of the vessel 3F and the cover 5F, there is such an effect that the vessel 3F and the cover 5F can be produced inexpensively with light weight. Furthermore, since the vessel 3F and the cover 5F are integrally molded with a simple structure of indentations and protrusions, there is such an effect that after preparation of a tympanic membrane regenerating agent, the preparation vessel for a tympanic membrane regenerating agent 1F can be washed and reused.

Note that in the preparation vessel for a tympanic membrane regenerating agent 1F, an easily removable cover seal for preventing infiltration of dust from the through-holes 65 before use of the preparation vessel for a tympanic membrane regenerating agent 1F may be applied to the holding portion 4F or the top plate 26 of the cover 5F.

Furthermore, as illustrated by imaginary lines in FIG. 13A, movement restricting protrusions 75 configured to restrict movement of the medicinal solution support 2 in the interior space S1 may be provided on a lower face of the holding portion 4F.

Furthermore, in present embodiment, when the cover 5F covers the vessel 3F with the respective long edges 53j and 64j of the flanges 53 and 64 aligned to each other, the cover 5F floats above the vessel 3F as illustrated in FIGS. 13A and 13B. However, for example, the fitting step 63 and the fitted step 52 may partially be fitted tightly together. According to such a configuration, there is such an effect that even before use of the preparation vessel for a tympanic membrane regenerating agent 1F, the holding portion 4F of the cover 5F can be affixed firmly to the vessel 3F in a state where the holding portion 4F is separated from the medicinal solution support 2.

The preferred embodiments of the present invention are described above by using the preparation vessels for a tympanic membrane regenerating agent 1A to 1F, but the present invention is not limited to the embodiments described above.

For example, in each of the preparation vessels for a tympanic membrane regenerating agent 1A, 1B and 1E, the cover 5A and the like are not mandatory as long as vertical movement of the medicinal solution support 2 can be prevented reliably by the weight of the holding member 4A or the like. Furthermore, vertical movement of the medicinal solution support 2 can be prevented reliably by providing a locking portion (not illustrated) on the holding member 4A or the like and providing a locked portion (not illustrated) on the vessel 3A or the like such that the holding member 4A or the like can be locked to the vessel 3A or the like to prevent upward movement of the holding member 4A or the like, and such that the lock of the holding member 4A or the like to the vessel 3A or the like can be released by pulling with at least certain force.

Furthermore, in the first, third and fourth embodiments, the preparation vessels for a tympanic membrane regenerating agent in which the holding members 4A and 4C have different forms are described, but the holding member applied to the present invention is not limited to these holding members. That is, the holding members 4A, 4C and 4D of the present invention may be configured in any manner as long as the holding members 4A, 4C and 4D suppress upward movement of the medicinal solution support 2 disposed in the housing portion S3 and the passage 25 through which the medicinal solution flows from the opening 6h toward the housing portion S3 is formed between the passage 25 and the vessel 3A or the like.

Furthermore, the structure of the holding portion 4F of the preparation vessel for a tympanic membrane regenerating agent 1F can also be applied to the cover 5A or the like in the preparation vessel for a tympanic membrane regenerating agent 1A and the like. That is, for example, a preparation vessel for a tympanic membrane regenerating agent may be configured such that, instead of the holding member 4A, a holding portion 4A molded integrally with the cover 5A by indenting the top plate 26 of the cover 5A inward is constituted, and such that the height of the body wall 9 of the vessel 3A is reduced as appropriate.

Furthermore, the preparation vessel for a tympanic membrane regenerating agent 1F preferably includes the fitting step 63, the fitted step 52 and the flanges 53 and 64, but may not include the fitting step 63, the fitted step 52 and the flanges 53 and 64. That is, the preparation vessel for a tympanic membrane regenerating agent 1F may include only the first projection 60 forming the interior space S1 and the second projection 67 forming the holding portion 4F covering the first projection 60.

Note that the vessel 3A and the like and the holding member 4A and the like, or the vessel 3A and the like, the holding member 4A and like and the cover 5A and the like described in the embodiments and the application examples can be used as the invention of the preparation jig for a tympanic membrane regenerating agent 1a (illustrated in FIG. 1) in which the medicinal solution support 2 is not set in advance. This preparation jig for a tympanic membrane regenerating agent 1a can be used in the same manner as the preparation vessel for a tympanic membrane regenerating agent 1A and the like by installing a medicinal solution support 2 separately prepared at the time of use in the housing portion S3 or the interior space S1 of the vessel 3F and the like, and the preparation jig for a tympanic membrane regenerating agent 1a exhibits the same actions, functions, and effects as those of the preparation vessel for a tympanic membrane regenerating agent 1A and the like except that the medicinal solution support 2 should be prepared separately.

The preparation vessels for a tympanic membrane regenerating agent 1A to 1F or the preparation jig for a tympanic membrane regenerating agent 1a and the like of the embodiments or the modification examples thereof described above may also be applied as other forms by combining different configurations as appropriate.

Furthermore, the vessel 3A and the like may also be made transparent or semi-transparent, and preferably the state of permeation of the medicinal solution into the medicinal solution support 2 installed in the vessel 3A and the like can be seen from the side face of the vessel 3A and the like.

Furthermore, the example in which the housing portion S3 or the interior space S1 is formed in a size enabling the medicinal solution support 2 to be easily grasped with tweezers (not illustrated) is described in the above embodiments, but the housing portion S3 or the interior space S1 may be formed in a size enabling the medicinal solution support 2 to be trimmed or the like in the housing portion S3 or the interior space S1.

Furthermore, the configuration in which only one medicinal solution support 2 is housed in the housing portion S3 or the interior space S1 is described in the above embodiments, but a plurality of medicinal solution supports 2 may be housed in the housing portion S3 or the interior space S1.

Figure 15:
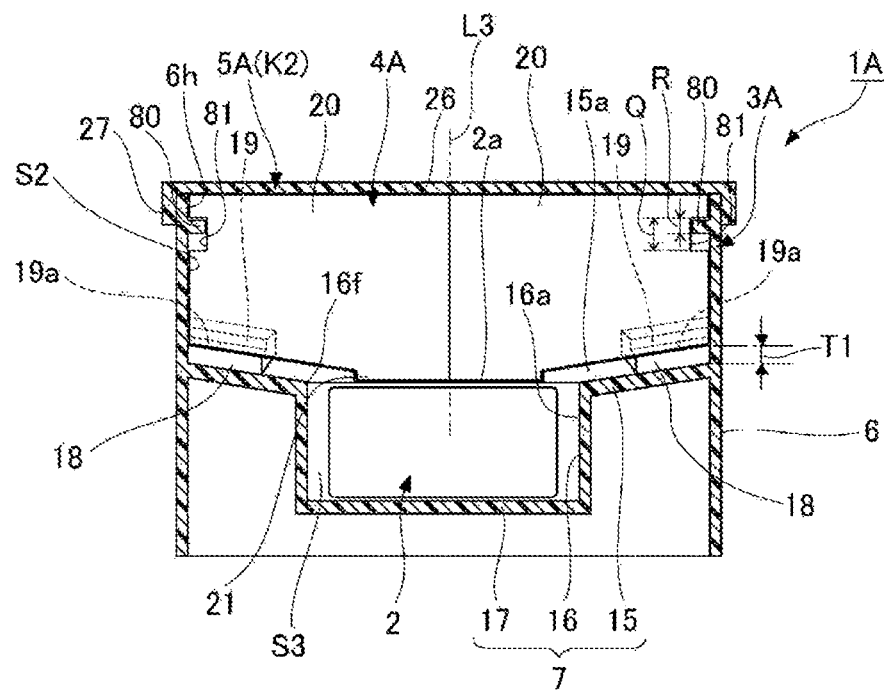
FIG. 15 is a partial longitudinal sectional view illustrating a modification example of the preparation vessel for a tympanic membrane regenerating agent according to the first embodiment of the present invention.

Moreover, in the preparation jig for a tympanic membrane regenerating agent 1a and the like described in the first, second, and fourth embodiments, engagement protrusions 80 and engagement indentations 81 configured to lock in the vertical direction and permit passage in the horizontal direction may be formed between the locking plate 20 and an inner circumferential wall of the vessel 3A as illustrated in FIG. 15.

Figure 16:
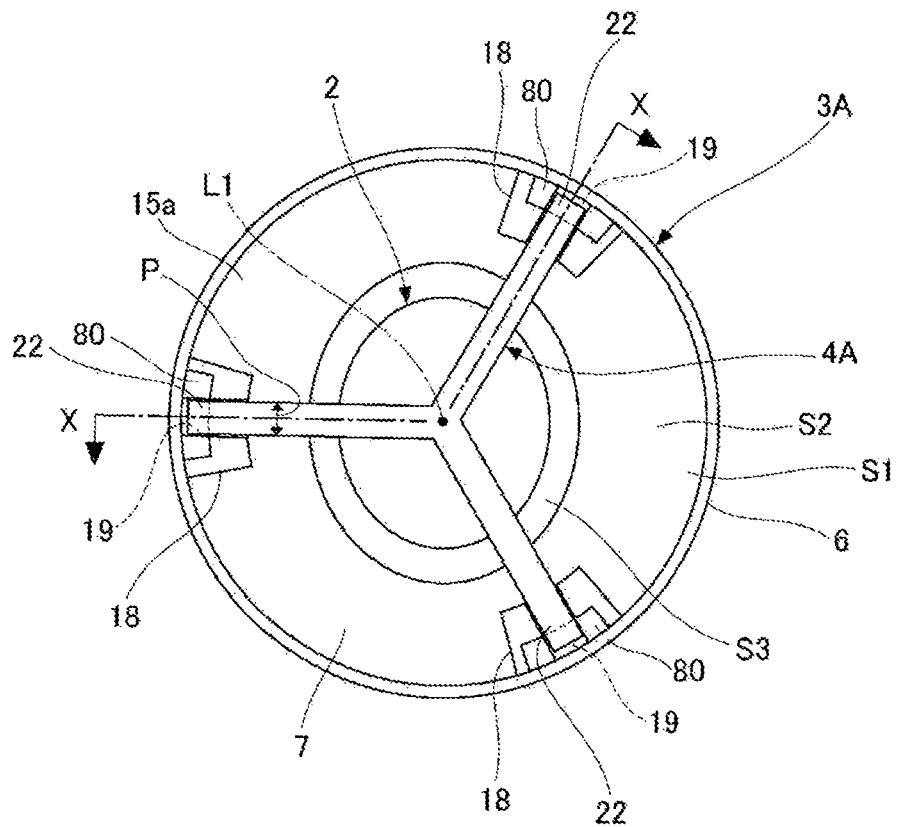
FIG. 16 is a plan view of a modification example of the preparation vessel for a tympanic membrane regenerating agent according to the first embodiment of the present invention, with a cover of the preparation vessel omitted.

Specifically, for example, the engagement protrusions 80 protruding from the side wall 6 to the inside are formed on the vessel 3A side and the like and spaced from one another in the peripheral direction as illustrated in FIG. 16, and the engagement indentations 81 each indented in a rectangular shape toward the axial line L3 and penetrating in the direction of thickness P are formed corresponding to the engagement protrusions 80 on the locking plate 20 as illustrated in FIG. 15.

In this case, a vertical dimension Q of each engagement indentation 81 is set to include at least a depth dimension of the groove 19 of the pedestal 18 added to a thickness dimension R of each engagement protrusion 80.

As illustrated in FIG. 16, a dimension in the peripheral direction of each engagement protrusion 80 is preferably set to be larger than the thickness dimension P of the locking plate 20 such that release of engagement between the engagement protrusions 80 and the engagement indentations 81 is not too easy.

In this case, the engagement protrusions 80 also have the functions of the upper side locking portion K1 and the lower side locking portion K2.

The preparation jig for a tympanic membrane regenerating agent 1a is configured in this manner, and thus, when the holding member 4A is inadvertently removed after the cover 5A has been removed, the holding member 4A can engage inner wall faces on the upper sides of the engagement protrusions 80. As a result, there is such an effect that attention can be called to the fact that the holding member 4A is mounted until the medicinal solution permeates the medicinal solution support 2.

On the other hand, after the medicinal solution permeates the medicinal solution support 2 and a tympanic membrane regenerating agent is prepared, the holding member 4A is rotated around the axial line L3 in a state where the holding member 4A disposed in the groove 19 of the pedestal 18 is lifted up from the groove 19. Engagement of the engagement protrusions 80 and the engagement indentations 81 is released, and the holding member 4A can be removed.

Note that in a case where the pedestals 18 are not formed in the vessel 3A and the like, since fitting into the groove 19 does not have to be taken into consideration, a dimension in the vertical direction of each engagement indentation 81 may be formed to match a dimension in the vertical direction of each engagement protrusion 80.

Figure 17:
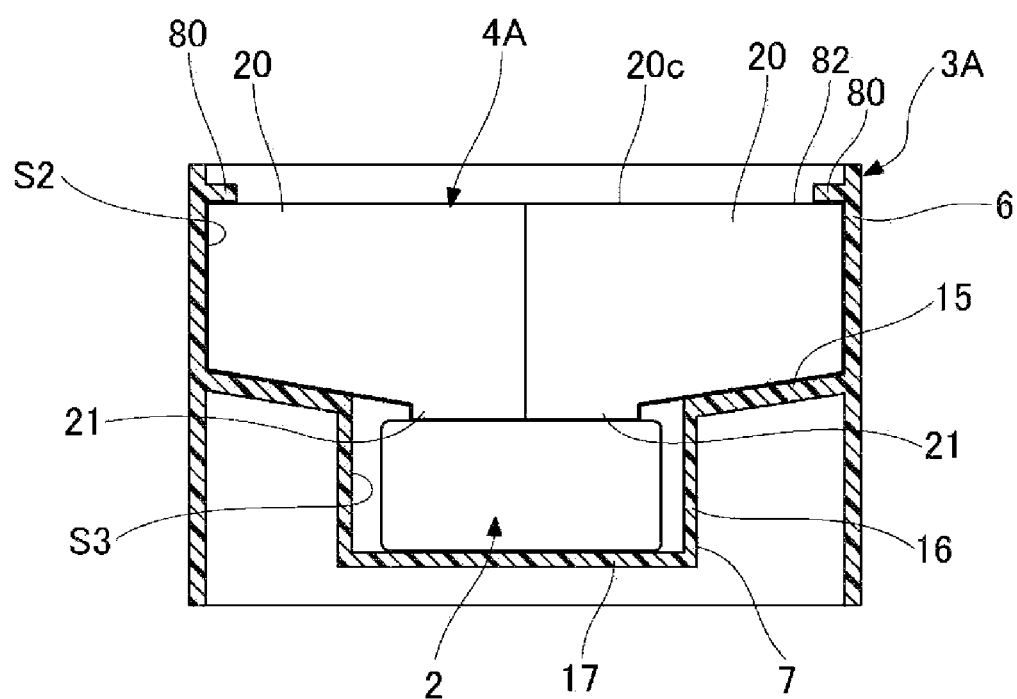
FIG. 17 is a partial longitudinal sectional view of a modification example of the preparation vessel for a tympanic membrane regenerating agent according to the first embodiment of the present invention, with a cover of the preparation vessel omitted.

Furthermore, as illustrated in FIG. 17, the upper face 20c of the holding member 4A may be configured as an engaged portion 82 for the engagement protrusions 80, and a dimension of the locking plate 20 of the holding member 4A may be set such that the engaged portion 82 is located below the engagement protrusions 80.

REFERENCE SIGNS LIST

1A to 1E Preparation vessel for a tympanic membrane regenerating agent
2 Medicinal solution support
3A to 3D Vessel
4A to 4D Holding member
5A Cover
6 Side wall
6h Opening
7 Bottom wall
25 Passage
30 Mounting portion
31 Reservoir
K1 Lower side locking portion
K2 Upper side locking portion
S1 Interior space
S2 Installation space
S3 Housing portion

The invention claimed is:

1. A preparation jig for a tympanic membrane regenerating agent comprising:
   a vessel comprising housing walls forming an interior space housing a medicinal solution support, and further comprising an opening opened in one direction and formed in the housing walls; and
   a holding portion disposed in the interior space and configured to hold the medicinal solution support housed in the vessel from an opening side thereof by moving the holding portion downwardly and upwardly toward an original position thereof,
   wherein a deep side of the interior space is a housing portion housing the medicinal solution support holding a medicinal solution,
   an opening side of the interior space corresponding to the opening side of the vessel is an installation space in which the holding portion is disposed, and
   the holding portion is configured to move downwardly so that air in the medicinal solution support is removed when the medicinal solution support holds the medicinal solution.

2. The preparation jig for a tympanic membrane regenerating agent according to claim 1,
   wherein a passage is formed in at least one of an inner wall face of the vessel or the holding portion, and the medicinal solution poured in from the opening flows into the housing portion through the passage, in a state where the holding portion is disposed in the installation space.

3. The preparation jig for a tympanic membrane regenerating agent according to claim 1,
   wherein a lower side locking portion that is configured to restrict movement of the holding portion toward the housing portion side is provided on the housing walls of the vessel.

4. The preparation jig for a tympanic membrane regenerating agent according to claim 1,
   wherein the housing portion comprises:
      a mounting portion on which the medicinal solution support is mounted; and
      a reservoir of the medicinal solution formed on the deep side of the mounting portion.

5. The preparation jig for a tympanic membrane regenerating agent according to claim 1,
   wherein the vessel comprises an upper side locking portion configured to prevent movement of the holding portion toward the opening side of the vessel.

6. The preparation jig for a tympanic membrane regenerating agent according to claim 1, further comprising a cover that comprises a top plate covering the opening of the vessel.

7. The preparation jig for a tympanic membrane regenerating agent according to claim 6,
   wherein the top plate comprises a concavity indented toward the installation space when the cover covers the vessel, and
   the concavity forms the holding portion.

8. The preparation jig for a tympanic membrane regenerating agent according to claim 7,
   wherein the vessel comprises a ring-shaped protruding wall that further surrounds the interior space, is placed on an outside of the housing walls, and protrudes to the opening side of the vessel, and
   the cover comprises a ring-shaped concavity formation wall forming, on a lower face side of the top plate, a ring-shaped concavity fitted onto the ring-shaped protruding wall, and
   the holding portion is formed inward of the concavity formation wall.

9. The preparation jig for a tympanic membrane regenerating agent according to claim 8, wherein the vessel further comprises:
   a fitting step overhanging further outward of the ring-shaped concavity formation wall, the fitting step being formed on an outside of the ring-shaped concavity formation wall; and
   a fitted step fitted into the fitting step, the fitted step overhanging outward of the ring-shaped protruding wall and being formed on the outside of the ring-shaped protruding wall.

10. The preparation jig for a tympanic membrane regenerating agent according to claim 9, wherein the vessel further comprises:
    a fitting protrusion formed on the fitting step; and
    a fitted protrusion fitted onto the fitting protrusion and formed on the fitted step.

11. The preparation jig for a tympanic membrane regenerating agent according to claim 10,
    wherein the fitting protrusion and the fitted protrusion are formed at positions where the fitting protrusion and the fitted protrusion are fitted together when the cover is oriented in one orientation around an axial line of the interior space relative to the vessel, and are not fitted together when the cover is oriented in any orientation other than the one orientation.

12. A preparation vessel for a tympanic membrane regenerating agent comprising: the vessel; and the holding portion described in claim 1,
   wherein the medicinal solution support is housed in the housing portion of the vessel.

13. The preparation vessel for a tympanic membrane regenerating agent according to claim 12, further comprising an openable pouch,
   wherein the medicinal solution is enclosed in the openable pouch held in the medicinal solution support and is housed in the interior space of the vessel.

\* \* \* \* \*